(12) United States Patent
Kamal et al.

(10) Patent No.: US 7,476,664 B2
(45) Date of Patent: Jan. 13, 2009

(54) BIS-2-DIFLUORO-PYRROLO[2,1-C][1,4] BENZODIAZEPINE DIMERS

(76) Inventors: Ahmed Kamal, Uppal Road, Hyderabad 500 007, Andhra Pradesh (IN); Depatla Rajasekhar Reddy, Uppal Road, Hyderabad 500 007, Andhra Pradesh (IN); Rajendar Rajendar, Uppal Road, Hyderabad 500 007, Andhra Pradesh (IN)

(*) Notice: Subject to any disclaimer, the term of this patent is extended or adjusted under 35 U.S.C. 154(b) by 0 days.

(21) Appl. No.: 11/715,592

(22) Filed: Mar. 7, 2007

(65) Prior Publication Data
US 2007/0249828 A1    Oct. 25, 2007

(51) Int. Cl.
*C07D 405/14* (2006.01)
*A61K 31/551* (2006.01)
*A61P 25/06* (2006.01)

(52) U.S. Cl. ........................... 514/220; 540/496
(58) Field of Classification Search ................. 540/496; 514/220
See application file for complete search history.

Primary Examiner—Bruck Kifle
(74) Attorney, Agent, or Firm—Arent Fox LLP

(57) ABSTRACT

The present invention provides a novel bis 2-difluoro pyrrolo [2,1-c][1,4]benzodiazepine of formula VII formula VII

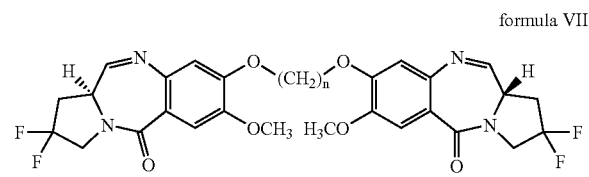

wherein, n is 3 to 10. novel bis 2-difluoro pyrrolo[2,1-c][1,4] benzodiazepine of formula VII exhibits biding affinity with calf thymus (CT) DNA at a molar ratio of 1:5 in aqueous sodium phosphate buffer at pH of about 7.00. The present invention further provides a process for the preparation of novel bis 2-difluoro pyrrolo[2,1-c][1,4]benzodiazepine of formula VII.

12 Claims, No Drawings

BIS-2-DIFLUORO-PYRROLO[2,1-C][1,4] BENZODIAZEPINE DIMERS

FIELD OF THE INVENTION

The present invention relates to novel bis-2-difluoro-pyrrolo[2,1-c][1,4]benzodiazepine dimmers of formula VII

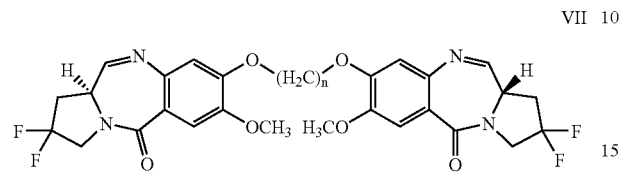

wherein, n is 3, 4, 5, 6, 7, 8, 9 or 10.

The present invention further relates to a process for the preparation of novel bis-2-difluoro-pyrrolo[2,1-c][1,4]benzodiazepines. More particularly, it provides a process for the preparation of 1,1'-{[(bisalkane-1,N-diyl)]dioxy}bis[(11aS)-2,2-difluoro-7-methoxy-1,2,3,11a-tetrahydro-5H-pyrrolo[2,1-c][1,4]benzodiazepin-5-one, with aliphatic chain length variations (n=3-10) for the compounds and it also describes the DNA-binding ability of these compounds.

BACKGROUND OF THE INVENTION

Pyrrolo[2,1-c][1,4]benzodiazepine antitumour antibiotics are commonly known as anthramycin class of compounds. In the last few decades, a growing interest has been shown in the development of new pyrrolo[2,1-c][1,4]benzodiazepines (PBDs). These PBDs are a family of sequence selective DNA-binding antitumour antibiotics that bind exclusively to the exocyclic N2-guanine in the minor groove of DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665; Kohn, K. W.; Speous, C. L. *J. Mol. Biol.*, 1970, 51, 551; Hurley, L. H. Gairpla, C.; Zmijewski, M. *Biochem. Biophys. Acta.*, 1977, 475, 521; Kaplan, D. J.; Hurley, L. H. *Biochemistry*, 1981, 20, 7572). All biologically active PBDs possess the (S) configuration at the chiral C11a position, which provides the molecule with a right-handed twist, which allows them to follow the curvature of the minor groove of B-form double-stranded DNA spanning three base pairs. Recently, PBD dimers have been developed that comprise two C2-exo-methylene-substituted DC-81 subunits tethered through their C-8 position via an inert propanedioxy linker (Gregson, S. J.; Howard, P. W.; Hartely, J. A.; Brooks, N. A.; Adams, L. J.; Jenkins, Kelland, L. R.; Thurston, D. E. *J. Med. Chem.*, 2001, 44, 737). A recent development has been the linking of two PBD units through their C-8 positions to give bisfunctional alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S.; Hurley, L. H. *J. Org. Chem.*, 1996, 61, 8141). Recently, a noncross-linking mixed imine-amide PBD dimers have been synthesized that have significant DNA binding ability and potent antitumour activitiy (Kamal, A.; Laxman, N.; Ramesh, G.; Ramulu, P; Srinivas, O U.S. Pat. No. 636,233. dt 26 Mar. 2002; Kamal, A.; Ramesh, G.; Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

The PBDs are of considerable current interest due to their ability to recognize and subsequently form covalent bonds to specific base sequences of double-stranded DNA. Naturally occurring pyrrolo[2,1-c][1,4]benzodiazepines belong to a group of antitumour antibiotics derived from *Streptomyces* species with family members including anthramycin, tomaymycin, sibiromycin, chicamycin, neothramycins A and B, and DC-81.

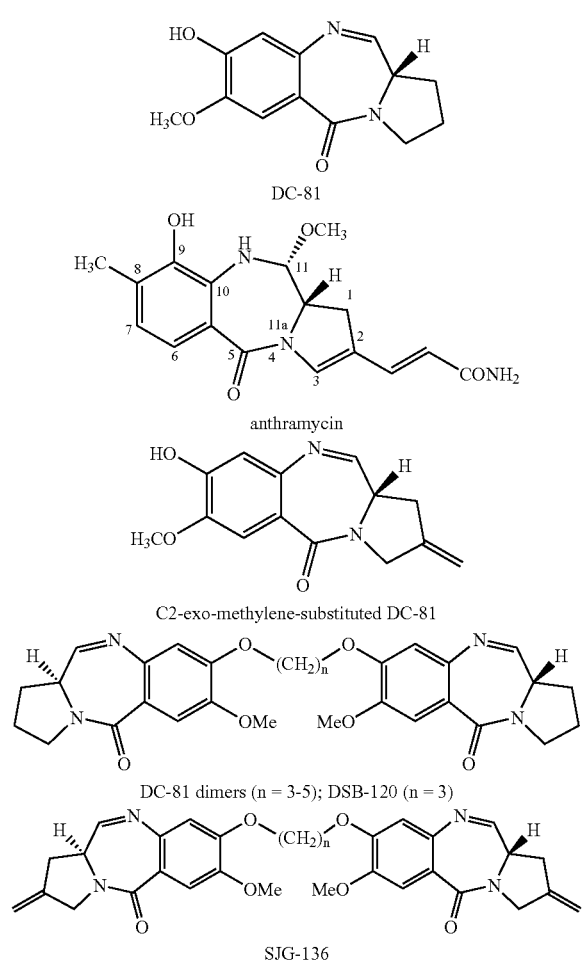

However, the clinical efficacy for these antibiotics is hindered by several limitations, such as poor water solubility and cardiotoxicity and development of drug resistance and metabolic inactivation.

OBJECTS OF THE INVENTION

The main object of the present invention is to provide new bis-2-difluoro pyrrolo[2,1-c][1,4]benzodiazepines as potential DNA-binding agents.

Another object of the invention is to provide a process for the preparation of novel bis-di-fluoro pyrrolo[2,1-c][1,4]benzodiazepines.

SUMMARY OF THE INVENTION

Accordingly, the present invention provides novel Bis-2-difluoro pyrrolo[2,1-c][1,4]benzodiazepine of formula VII formula VII

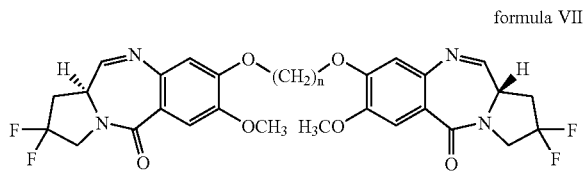

wherein, n varies from 3 to 10.

In an embodiment of the present invention the novel bis-2-di-fluoro pyrrolo[2,1-c][1,4]benzodiazepine as claimed in claim 1 is represented by a group of compounds comprising:

1,1'-{[(propane-1,3-diyl)]dioxy}bis[(11aS)-2,2-difluoro-7-methoxy-1,2,3,11a-tetrahydro-5H-pyrrolo[2,1-c][1,4]benzodiazepin-5-one]} (VII a)

1,1'-{[(butane-1,4-diyl)]dioxy}bis[(11aS)-2,2-difluoro-7-methoxy-1,2,3,11a tetra-hydro-5H-pyrrolo[2,1-c][1,4]benzodiazepin-5-one]} (VIIb)

1,1'-{[(pentane-1,5-diyl)]dioxy}bis[(11aS)-2,2-difluoro-7-methoxy-1,2,3,11a-tetra-hydro-5H-pyrrolo[2,1-c][1,4]benzodiazepin-5-one]} (VIIc)

In yet another embodiment the novel bis-2-di-fluoro pyrrolo[2,1-c][1,4]benzodiazepine of formula VIIa-c exhibits biding affinity with calf thymus (CT) DNA at a molar ratio of about 1:5 in aqueous sodium phosphate buffer at pH of about 7.00.

The present invention further provides a process for the preparation of novel Bis-2-difluoro pyrrolo[2,1-c][1,4]benzodiazepine of formula VII formula VII

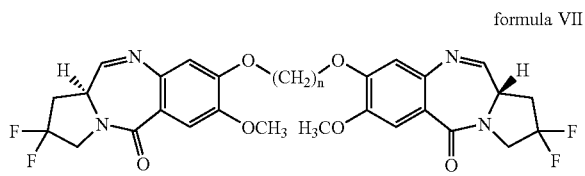

wherein, n varies from 3 to 10 and the said process comprising the steps of:

(a) preparing (2S)-N-(4-hydroxy-5-methoxy-2-nitrobenzoyl)-4,4 difluoropyrrolidine 2-carboxaldehyde diethylthioacetal of formula IV by known method,

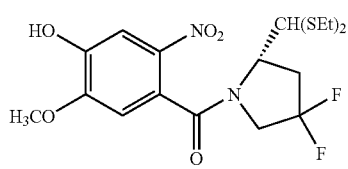

(b) reacting the compound of formula IV with dibromoalkane in a dry aprotic water miscible organic solvent, in the presence of mild inorganic base, under reflux, for a period of about 48 hours, followed by pouring the resultant reaction mixture on to the water and extracting and purifying the resultant crude product by known method to obtain the compound 1,1'-{[(alkane diyl)dioxy]bis[2-nitro-5-methoxy-1,4-phenylene)carbonyl]}bis[4,4-difluoro pyrrolidine-2-carboxaldehyde diethyl thioacetal] of formula V,

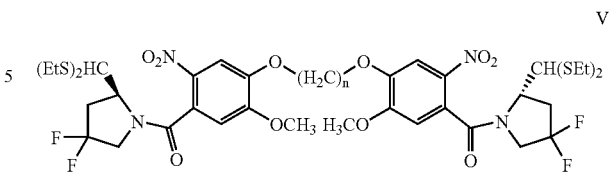

wherein, n varies from 3 to 10

(c) reducing the compound of formula V obtained in step (b) with $SnCl_2$ in an organic solvent, under reflux, for a period of 1-2 hours, at a pH of about 8 in the presence of saturated alkalibicarbonate solution, followed by extraction with an organic solvent and drying the resultant organic phase over $Na_2SO_4$ and evaporating the solvent under vacuum to obtain the resultant compound of 1,1'-{[(alkane diyl)dioxy]bis[2-amino-5-methoxy-1,4-phenylene)carbonyl]}bis[4,4-difluoro pyrrolidine-2-carboxaldehyde diethyl thioacetal] of formula VI,

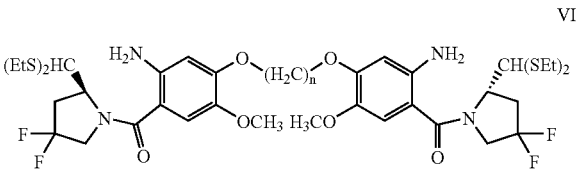

wherein, n varies from 3 to 10

(d) reacting the compound of formula VI with mercurous chloride and calcium carbonate in the presence of an aqueous organic solvent wherein organic solvent to water ratio is about 4:1, under stirring, at a temperature of 25-30° C., for a period of about 12 hours, followed by the evaporation of organic layer to obtain the crude residue and purifying the residue by known method to obtain the desired product of 1,1'-{[(bisalkane-1,N-diyl)]dioxy}bis[(11aS)-2,2-difluoro-7-methoxy-1,2,3,11a-tetrahydro-5H-pyrrolo[2,1-c][1,4]benzodiazepine-5-one of formula VII (a-c).

In yet another embodiment the dibromoalkane used in step(a) is selected from the group consisting of 1,3-dibromopropane, 1,4-dibromobuatne and 1,5-dibromopentane.

In yet another embodiment the dry organic solvent used in step(b) is selected from acetone, acetonitrile and DMF.

In yet another embodiment the mild inorganic base used in step(b) is selected from $K_2CO_3$, $CsCO_3$ and $BaCO_3$.

In yet another embodiment the compound of formula V used in step(b) is selected from the group consisting of 1,1'-{[(Propane-1,3 diyl)dioxy]bis[2-nitro-5-methoxy-1,4-phenylene)carbonyl]}bis[4,4-difluoropyrrolidine-2-carboxaldehyde diethyl thioacetal (Va);

1,1'-{[Butane-1,4-diyl)dioxy]bis(2-nitro-5-methoxy-1,4-phenylene)carbonyl]}bis[4,4-difluoropyrrolidine-2-carboxaldehyde diethylthioacetal] (Vb) and 1,1'-{[Pentane-1,5-diyl)dioxy]bis(2-nitro-5-methoxy-1,4-phenylene)carbonyl]}bis[4,4-difluoropyrroilidine-2-carboxaldehyde diethylthioacetal] (Vc).

In yet another embodiment the the compound of formula VI obtained in step (c) is selected from the group consisting of 1,1'-{[(Propane-1,3diyl)dioxy]bis[2-amino-5-methoxy-1,4-pheny-lene)carbonyl]}bis[4,4-difluoropyrrolidine-2-carboxaldehyde diethylthioacetal (VIa); 1,1'-{[Butane-1,4-diyl)dioxy]bis(2-amino-5-methoxy-1,4-phenylene)carbonyl]}bis

[4,4-difluoropyrrolidine-2-carboxaldehyde diethylthioacetal (VIb) and 1,1'-{[Pentane-1,5-diyl)dioxy]bis(2-amino-5-methoxy-1,4-phenylene)carbonyl]}bis[4,4-difluoropyrrolidine-2-carboxaldehyde diethylthioacetal (VIc).

In yet another embodiment the organic solvent used in step (c) is ethyl acetate.

In yet another embodiment the alkalibicarbonate used in step(c) is selected from sodiumbicarbonate.

In yet another embodiment organic solvent used in step(c) is methanol.

In yet another embodiment organic solvent used in step(d) is acetonitrile.

In yet another embodiment 1,1'-{[(bisalkane-1,N-diyl)]dioxy}bis[(11aS)-2,2-difluoro-7-methoxy-1,2,3,11a-tetrahydro-5H-pyrrolo[2,1-c][1,4]benzodiazepin-5-one of formula VII obtained in step (d) is represented by a group of compounds comprising:

1,1'-{[(propane-1,3-diyl)]dioxy}bis[(11aS)-2,2-difluoro-7-methoxy-1,2,3,11a-tetrahydro-5H-pyrrolo[2,1 c][1,4]benzodiazepin-5-one]} (VII a);

1,1'-{[(butane-1,4-diyl)]dioxy}bis[(11aS)-2,2-difluoro-7-methoxy-1,2,3,11a tetra-hydro-5H-pyrrolo[2,1-c][1,4] benzodiazepin-5-one]} (VIIb) and 1,1'-{[(pentane-1,5-diyl)]dioxy}bis[(11aS)-2,2-difluoro-7-methoxy-1,2,3, 11a-tetra-hydro-5H-pyrrolo[2,1-c][1,4]benzodiazepin-5-one]} (VIIc)

In still another embodiment bis-difluoro substituted PBD dimers (VIIa-c) exhibits biding affinity with calf thymus (CT) DNA at a molar ratio of about 1:5 in aqueous sodium phosphate buffer at pH of about 7.00.

DETAILED DESCRIPTION OF THE INVENTION

The present process provides a process for the preparation of bis 2-difluoro pyrrolo[2,1-c][1,4]benzodiazepines of formula VII of the drawing accompanying the specification where n is 3 to 10 which comprises: methyl (2S)-N-[4-benzyloxy-5-methoxy-2-nitrobenzoyl]-4,4-difluoropyrrolidine-2-carboxylate of formula I was reduced with DIBAL-H in presence of organic solvent like $CH_2Cl_2$ cooled to –78° C. for a period of 45 min isolating methyl (2S)-N-[4-benzyloxy-5-methoxy-2-nitrobenzoyl]-4,4-difluoropyrrolidine-2-carboxaldehyde II by conventional methods, protecting the above compound of formula II with EtSH in presence of organic solvent at room temperature isolating the (2S)-N-[4-benzyloxy-5-methoxy-2-nitrobenzoyl]-4,4-difluoropyrrolidine-2-carboxaldehyde diethylthioacetal III by known methods, reacting the above said thio compound of formula III with known debenzylating agents in a conventional manner to give (2S)-N-[4-hydroxy-5-methoxy-2-nitrobenzoyl]-4,4-difluoropyrrolidine-2-carboxaldehyde-diethylthioacetal of formula IV.

Accordingly, the present process provides a process for preparation of bis 2-difluoropyrrolo[2,1-c][1,4]benzodiazepines of formula of the drawing accompanying the specification where n is 3 to 10 which comprises: reacting (2S)-N-[4-hydroxy-5-methoxy-2-nitrobenzoyl]-4,4-difluoro-2-carboxaldehyde diethylthioacetal of formula IV with dibromoalkanes in an aprotic water miscible organic solvents like acetone, acetonitrile, and DMF in presence of a mild inorganic bases like $K_2CO_3$, $CsCO_3$ and $BaCO_3$ upto refluxing temperature for a period of 48 hours, isolating 1,1'-{[(alkane-1,N-diyl)dioxy}bis[(2-nitro-5-methoxy-1,4-phenylene)carbonyl]bis[4,4-difluoropyrrolidin-2-carboxaldehyde diethylthioacetal] of formula V where n is 3-10 by conventional methods, reducing the above nitro compounds of formula V with $SnCl_2.2H_2O$ in presence of organic solvent up to a reflux temperature, isolating the 1,1-{[(alkane-1,N-diyl)dioxy}bis[(2-amino-5-methoxy-1,4-phenylene)carbonyl]]bis[4,4-difluoropyrrolidin-2-carboxaldehyde diethylthioacetal]] of formula VI where n is 3-10 by known methods, reacting the above said amino compound of formula VI with known deprotecting agents in a conventional manner to give novel bis 2-difluoropyrrolo[2,1-c][1,4]benzodiazepines of formula VII wherein n is as stated above.

The precursor, methyl (2S)-N-(4-benzyloxy-5-methoxy-2-nitrobenzoyl)-4,4-difluoroypyrrolidine-2-carboxylate of formula I (intermediates of DC-81) was prepared by literature methods (Dc Luca, L.; Giacomelli, G.; Porcheddu, A. *Org. Lett.* 2001, 3, 3041; Demange, L.; Ménez, A.; Dugave, C. *Tetrahedron Lett.* 1998, 39, 1169; Kamal, A.; Reddy, P. S. M. M.; Reddy, D. R. *Bioorg. Med. Chem. Lett.* 2004, 14, 2669; Kamal, A.; Reddy, P. S. M. M.; Reddy, D. R.; Laxman, E.; Murthy, Y. L. N. *Bioorg. Med. Chem. Lett.* 2004, 14, 5699; Thurston, D. E.; Murthy, V. S.; Langley, D. R.; Jones, G. B. *Synthesis,* 1990, 81).

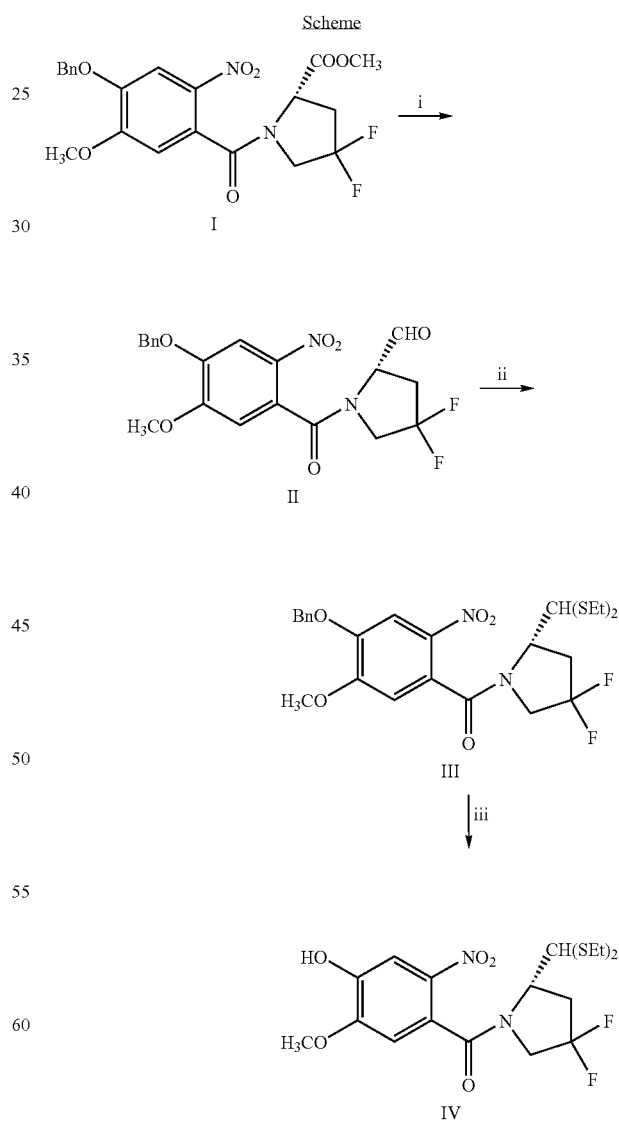

Reagents and conditions: (i) DIBAL-H, $CH_2Cl_2$, -78° C.; (ii) EtSH-TMS-Cl, $CH_2Cl_2$; (iii) EtSH-$BF_3OEt_2$, $CH_2Cl_2$

Scheme

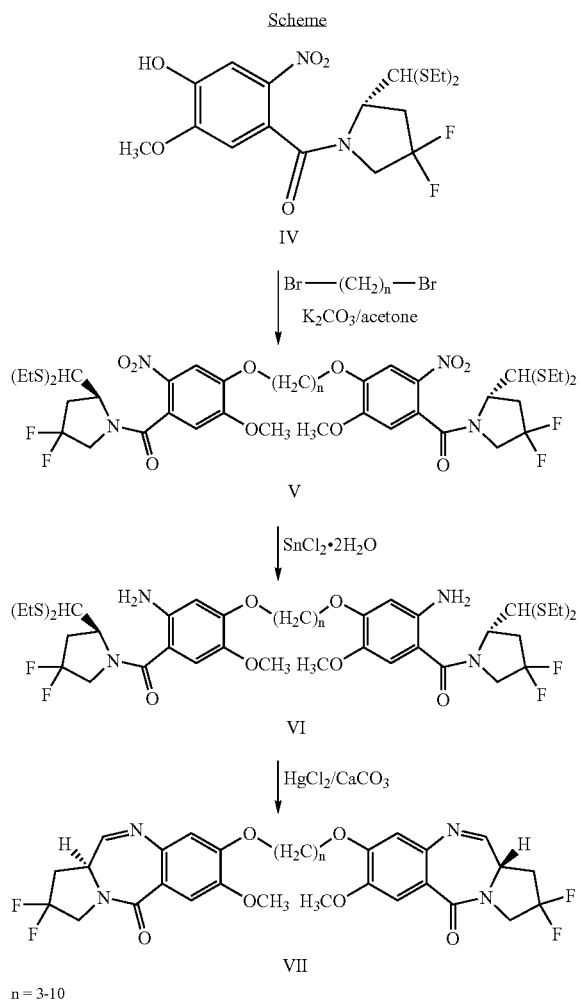

n = 3-10

Some representative compounds of formula VII of present invention are given below:
1) 1,1'-{[(propane-1,3-diyl)dioxy]bis[(11aS)-2,2-difluoro-7-methoxy-1,2,3,11a-tetra-hydro-5H-pyrrolo[2,1-c][1,4]benzodiazepin-5-one]}
2) 1,1'-{[(butane-1,4-diyl)dioxy]bis[(11aS)-2,2-difluoro-7-methoxy-1,2,3,11a-tetra-hydro-5H-pyrrolo[2,1-c][1,4]benzodiazepin-5-one]}
3) 1,1'-{[(pentane-1,5-diyl)dioxy]bis[(11aS)-2,2-difluoro-7-methoxy-1,2,3,11a-tetra-hydro-5H-pyrrolo[2,1-c][1,4]benzodiazepin-5-one]}

These new analogues of pyrrolo[2,1-c][1,4]benzodiazepine dimers substituted at C2-position have shown promising DNA-binding ability. The molecules synthesized are of immense biological significance with potential sequence selective DNA-binding property. This resulted in design and synthesis of new congeners as illustrated in the scheme, which comprise:
1. The difluoro substitution at C2-position of DC-81 intermediates.
2. The ether linkage between two difluoro DC-81 monomers at C-8 position.
3. Refluxing the reaction mixture for 24-48 h.
4. Synthesis of difluoro PBD antitumour antibiotic dimer imines.
5. Purification by column chromatography using different solvents like ethyl acetate, hexane.

The following examples are given by way of illustration and therefore should not be construed to the present limit of the scope of invention.

EXAMPLE 1

A solution of (2S)-N-(4-hydroxy-5-methoxy-2-nitrobenzoyl)-4,4-difluoropyrrolidine 2-carboxaldehyde diethylthioacetal IV (1 mmol), 1,3-dibromopropane (0.5 mmol) and $K_2CO_3$ (3 mmol) in dry acetone (40 ml) was refluxed for 48 h. After the completion of reaction as indicated by TLC, EtOAc-hexane (6:4), the reaction mixture was poured on to the water and then extracted with ethyl acetate. Evaporation of the organic layer gave the crude product, which was further purified by column chromatography on silica gel eluting with EtOAc-hexane (1:1) to give the pure 1,1'-{[(Propane-1,3diyl)dioxy]bis[2-nitro-5-methoxy-1,4-phenylene)carbonyl]}bis[4,4-difluoropyrrolidine-2-carboxaldehyde diethylthioacetal] V.

$H^1$ NMR ($CDCl_3$, 200 MHz): □ 1.25-1.40 (m, 12H), 2.15-2.50 (m, 6H), 2.60-2.95 (m, 8H), 3.40-3.85 (m, 4H), 3.95 (s, 6H), 4.25-4.45 (t, 4 H), 4.75 (d, J=4.0 Hz, 2H), 4.82-4.95 (m, 2H), 6.75 (s, 2H), 7.70 (s, 2H). FAB MASS: 914 (M+H)

1,1'-{[(Propane-1,3 diyl)dioxy]bis[2-nitro-5-methoxy-1,4-phenylene)carbonyl]}bis[4,4-difluoropyrrolidine-2-carboxaldehyde diethyl thioacetal] V (1.0 mmol) was dissolved in methanol (10 mL) and to this was added $SnCl_2.2H_2O$ (5.0 mmol) and was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude 1,1'-{[(Propane-1,3 diyl)dioxy]bis[2-amino-5-methoxy-1,4-phenylene)carbonyl]}bis[4,4-difluoropyrrolidine-2-carboxaldehyde diethylthioacetal] VI.

A solution of the 1,1'-{[(Propane-1,3 diyl)dioxy]bis[2-amino-5-methoxy-1,4-pheny-lene)carbonyl]}bis[4,4-difluoropyrrolidine-2-carboxaldehyde diethylthioacetal] VI (1 mmol), $HgCl_2$ (6.0 mmol) and $CaCO_3$ (6.0 mmol) in $CH_3CN$/$H_2O$ (4:1) was stirred at room temperature for 12 h until TLC (EtOAc), indicated complete loss of starting material. Then the organic layer was evaporated in vacuum and the residue was diluted with EtOAc. To this, saturated $NaHCO_3$ solution was added slowly at room temperature and the mixture was filtered through celite and washed with ethyl acetate. The filterate was evaporated in vacuum to get crude 1,1'-{[(propane-1,3-diyl)]dioxy}bis[(11aS)-2,2-difluoro-7-methoxy-1,2,3,11a-tetrahydro-5H-pyrrolo[2,1-c][1,4]benzodiazepin-5-one] of formula VIIa, which was further purified by column chromatography on silica gel eluting with ethyl acetate.

$H^1$ NMR ($CDCl_3$, 200 MHz): □ 1.85-2.05 (m, 2H), 2.20-2.65 (m, 4H), 3.52-3.85 (m, 6H), 3.94 (s, 6H), 4.00-4.25 (m, 4H), 6.80 (s, 2H), 7.44 (s, 2H), 7.79 (d, 2H, J=5.0 Hz). MS (FAB): 605 [M+1]$^+$.

EXAMPLE 2

A solution of (2S)-N-(4-hydroxy-5-methoxy-2-nitrobenzoyl)-4,4-difluoropyrrolidine 2-carboxaldehyde diethylthioacetal IV (1 mmol), 1,4-dibromobutane (0.5 mmol) and $K_2CO_3$ (3 mmol) in dry acetone (20 ml) was refluxed for 48 h. After the completion of reaction as indicated by TLC, EtOAc-hexane (6:4), the reaction mixture was poured on to the water and then extracted with ethyl acetate. Evaporation of the organic layer gave the crude product, which was further purified by column chromatography on silica gel eluting with EtOAc-hexane (1:1) to give the pure 1,1'-{[Butane-1,4-diyl)dioxy]bis(2-nitro-5-methoxy-1,4-phenylene)carbonyl]}bis[4,4-difluoropyrroilidine-2-carboxaldehyde diethylthioacetal] V.

H$^1$ NMR (CDCl$_3$, 200 MHz): □1.29-1.40 (m, 12H), 2.10-2.60 (m, 8H), 2.70-2.90 (m, 8H), 3.40-3.70 (m, 4H), 3.96 (s, 6H), 4.25 (t, 4 H), 4.70 (d, 2H), 4.75-4.90 (m, 2H), 6.65 (s, 2H), 7.70 (s, 2H). FAB MASS: 928 (M+H)

1,1'-{[Butane-1,4-diyl)dioxy]bis(2-nitro-5-methoxy-1,4-phenylene)carbonyl]}bis[4,4-difluoropyrrolidine-2-carboxaldehyde diethylthioacetal] of formula V (1.0 mmol) was dissolved in methanol (10 ml) and added SnCl$_2$.2H$_2$O (5.0 mmol) was refluxed for 1.5 h. The reaction mixture was then carefully adjusted to pH 8 with saturated NaHCO$_3$ solution and then extracted with ethyl acetate (3×20 ml). The combined organic phase was dried over Na$_2$SO$_4$ and evaporated under vacuum to afford the crude of pure 1,1'-{[Butane-1,4-diyl)dioxy]bis(2-amino-5-methoxy-1,4-phenylene)carbonyl]}bis[4,4-difluoropyrrolidine-2-carboxaldehyde diethylthioacetal of formula VI.

A solution of 1,1'-{[Butane-1,4-diyl)dioxy]bis(2-amino-5-methoxy-1,4-phenylene)carbonyl]}bis[4,4-difluoropyrrolidine-2-carboxaldehyde diethylthioacetal of formula VI (1 mmol), HgCl$_2$ (6.0 mmol) and CaCO$_3$ (6.0 mmol) in CH$_3$CN/H$_2$O (4:1) was stirred at room temperature for 12 h until TLC (EtOAc), indicated complete loss of starting material. Then organic layer was evaporated in vacuum and the residue was diluted with EtOAc. To this, saturated NaHCO$_3$ solution was added slowly at room temperature and the mixture was filtered through celite and washed with ethyl acetate. The filtrate was evaporated in vacuum to get crude 1,1'-{[(butane-1,4-diyl)]dioxy}bis[(11aS)-2,2-difluoro-7-methoxy-1,2,3,11a-tetrahydro-5H-pyrrolo[2,1-c][1,4]benzodiazepin-5-one VIIb, which was further purified by column chromatography on silica gel eluting with ethyl acetate.

H$^1$ NMR (CDCl$_3$, 200 MHz): □ 1.85-2.15 (m, 4H), 2.25-2.85 (m, 4H), 3.50-3.83 (m, 6H), 3.93 (s, 6H), 4.01-4.35 (m, 4H), 6.80 (s, 2H), 7.43 (s, 2H), 7.78 (d, 2H, J=5.2 Hz). MS (FAB): 619 [M+1]$^+$.

EXAMPLE 3

A solution of (2S)-N-(4-hydroxy-5-methoxy-2-nitrobenzoyl)-4,4-difluoropyrrolidine 2-carboxaldehyde diethylthioacetal IV (1.0 mmol), 1,5-dibromopentane (0.5 mmol) and K$_2$CO$_3$ (3 mmol) in dry acetone (20 ml) was refluxed for 48 h. After the completion of reaction as indicated by TLC, EtOAc-hexane (6:4), the reaction mixture was poured on to the water and then extracted with ethyl acetate. Evaporation of the organic layer gave the crude product, which was further purified by column chromatography on silica gel eluting with EtOAc-hexane (1:1) to give the pure 1,1'-{[Pentane-1,5-diyl)dioxy]bis(2-nitro-5-methoxy-1,4-phenylene)carbonyl]}bis[4,4-difluoropyrroilidine-2-carboxaldehyde diethyl thioacetal V.

H$^1$ NMR (CDCl$_3$, 200 MHz): □ 1.35-1.45 (m, 12H), 1.75-1.85 (m, 6H), 1.95-2.95 (m, 12H), 3.50-3.60 (m, 4H), 4.05 (s, 6H), 4.20 (m, 4H), 4.85-4.95 (m, 4H), 6.80 (s, 2H), 7.75 (s, 2H). FAB MASS: 942 (M+H)

1,1'-{[Pentane-1,5-diyl)dioxy]bis(2-nitro-5-methoxy-1,4-phenylene)carbonyl]}bis[4,4-difluoropyrroilidine-2-carboxaldehyde diethylthioacetal] of formula V (1.0 mmol) was dissolved in methanol (10 ml) and to it was added SnCl$_2$.2H$_2$O (5.0 mmol) and was refluxed for 1.5 h. The reaction mixture was then carefully adjusted to pH 8 with saturated NaHCO$_3$ solution and then extracted with ethyl acetate (3×20 ml). The combined organic phase was dried over Na$_2$SO$_4$ and evaporated under vacuum to afford the crude 1'-{[Pentane-1,5-diyl)dioxy]bis(2-amino-5-methoxy-1,4-phenylene)carbonyl]}bis[4,4-difluoropyrrolidine-2-carboxaldehyde diethylthioacetal of formula VI.

A solution of 1,1'-{[Pentane-1,5-diyl)dioxy]bis(2-amino-5-methoxy-1,4-phenylene)carbonyl]}bis[4,4-difluoropyrrolidine-2-carboxaldehyde diethylthioacetal of formula VI (1 mmol), HgCl$_2$ (6.0 mmol) and CaCO$_3$ (6.0 mmol) in CH$_3$CN/H$_2$O (4:1) was stirred at room temperature for 12 h until TLC (EtOAc) indicated complete loss of starting material. Then organic layer was evaporated in vacuum and the residue was diluted with EtOAc. To this, saturated NaHCO$_3$ solution was added slowly at room temperature and the mixture was filtered through celite and washed with ethyl acetate. The filtrate was evaporated in vacuum to get crude 1,1'-{[(pentane-1,5-diyl)]dioxy}bis[(11aS)-2,2-difluoro-7-methoxy-1,2,3,11a-tetrahydro-5H-pyrrolo[2,1-c][1,4]benzodiazepin-5-one VIIc, which was further purified by column chromatography on silica gel eluting with ethyl acetate.

H$^1$ NMR (CDCl$_3$, 200 MHz): □ 1.80-2.05 (m, 6H), 2.10-2.40 (m, 4H), 2.70-2.95 (m, 6H), 3.93 (s, 6H), 3.99-4.25 (m, 4H), 6.80 (s, 2H), 7.45 (s, 2H), 7.79 (d, 2H, J=5.1 Hz). MS (FAB): 633 [M+1]$^+$.

Thermal Denaturation Studies

The DNA binding affinity of the novel C2 di-fluoro PBD dimers (VIIa-c) was investigated by thermal denaturation studies using calf thymus (CT) DNA (Jones, G. B.; Davey, C. L.; Jenkins, T. C.; Kamal, A.; Kneale, G. G.; Neidle, S.; Webster, G. D.; Thurston, D. E. *Anti-Cancer Drug Des.* 1990, 5, 249. McConnaughie, A. W.; Jenkins, T. C. *J. Med. Chem.* 1995, 38, 3488). The studies for these compounds (VIIa-c) were carried out by DNA/ligand molar ratios of 5:1. The increase in the helix melting temperature. ($\Delta T_m$) for each compound was examined after 0, 18 and 36 h incubation at 37° C. Data for DC-81 and DSB-120 are included in Table 1 for comparison. The naturally occurring DC-81 gives a $\Delta T_m$ of 0.7° C. and whereas synthetic DC-81 dimer (DSB-120) gives a $\Delta T_m$ of 15.1° C. under identical experimental conditions (Table 1).

TABLE 1

Thermal denaturation data for C2-difluoro substituted PBD dimers with calf thymus (CT) DNA.

| PBD Dimers | [PBD]:[DNA] molar ratio[b] | $\Delta T_m$ (° C.)[a] after incubation at 37° C. for | | |
|---|---|---|---|---|
| | | 0 h | 18 h | 36 h |
| VIIa | 1:5 | 13.1 | 23.4 | 27.5 |
| VIIb | 1:5 | 4.2 | 23.4 | 24.7 |
| VIIc | 1:5 | 18.9 | 24.5 | 28.4 |
| DSB-120 | 1:5 | 10.2 | 15.1 | 15.4 |
| DC-81 | 1:5 | 0.3 | 0.7 | 0.7 |

[a]For CT-DNA alone at pH 7.00 ± 0.01, T$_m$ = 69.6° C. ± 0.01 (mean value from 10 separate determinations), all $\Delta T_m$ values are ± 0.1-0.2° C.
[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

We claim:
1. A bis-2-difluoro-pyrrolo[2,1-c][1,4]benzodiazepine compound of formula VII formula VII

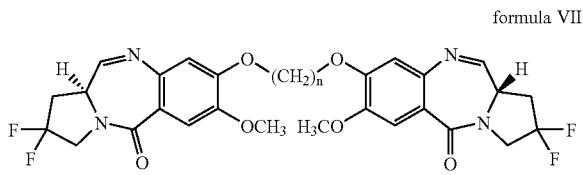

wherein n varies from 3 to 10.

2. The compound as claimed in claim 1, wherein the compound of formula VII is selected from the group consisting of:
- 1,1'-{[(propane-1,3-diyl)]dioxy}bis[(11aS)-2,2-difluoro-7-methoxy-1,2,3,11a-tetrahydro-5H-pyrrolo[2,1-c][1,4]benzodiazepin-5-one]} (VIIa);
- 1,1'-{[(butane-1,4-diyl)]dioxy}bis[(11aS)-2,2-difluoro-7-methoxy-1,2,3,11a-tetra-hydro-5H-pyrrolo[2,1-c][1,4]benzodiazepin-5-one]} (VIIb); and
- 1,1'-{[(pentane-1,5-diyl)]dioxy}bis[(11aS)-2,2-difluoro-7-methoxy-1,2,3,11a-tetra-hydro-5H-pyrrolo[2,1-c][1,4]benzodiazepin-5-one]} (VIIc).

3. A process for preparing bis-2-difluoro-pyrrolo[2,1-c][1,4]benzodiazepine compounds of formula VII formula VII

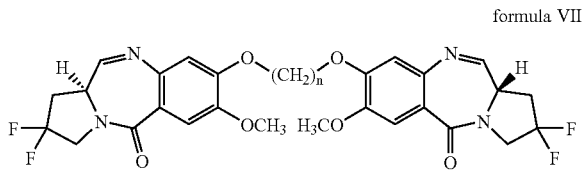

wherein n varies from 3 to 10 and the process comprises the steps of:

(a) preparing (2S)-N-(4-hydroxy-5-methoxy-2-nitrobenzoyl)-4,4difluoropyrrolidine 2-carboxaldehyde diethylthioacetal of formula IV by known method,

IV

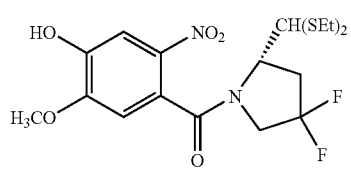

(b) reacting the compound of formula IV with dibromoalkane in a dry aprotic water miscible organic solvent, in the presence of mild inorganic base, under reflux, for a period of about 48 hours, followed by pouring the resultant reaction mixture on to the water and extracting and purifying the resultant crude product by known method to obtain the compound 1,1'-{[(alkane diyl)dioxy]bis[2-nitro-5-methoxy-1,4-phenylene)carbonyl]}bis[4,4-difluoropyrrolidine-2-carboxaldehyde diethyl thioacetal] of formula V, wherein n varies from 3 to 10,

V

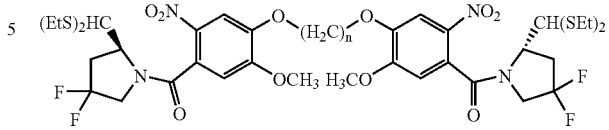

(c) reducing the compound of formula V obtained in step (b) with $SnCl_2$ in an organic solvent, under reflux, for a period of 1-2 hours, at a pH of about 8 in the presence of saturated alkali bicarbonate solution, followed by extraction with an organic solvent and drying the resultant organic phase over $Na_2SO_4$ and evaporating the solvent under vacuum to obtain the resultant compound of 1,1'-{[(alkane diyl)dioxy]bis[2-amino-5-methoxy-1,4-phenylene)carbonyl]}bis[4,4-difluoro pyrrolidine-2-carboxaldehyde diethyl thioacetal] of formula VI, wherein n varies from 3 to 10

VI

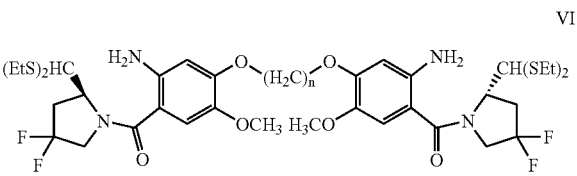

(d) reacting the compound of formula VI with mercurous chloride and calcium carbonate in the presence of an aqueous organic solvent wherein organic solvent to water ratio is about 4:1, under stirring, at a temperature of 25-30° C., for a period of about 12 hours, followed by the evaporation of organic layer to obtain the crude residue and purifying the residue by known method to obtain the desired product of 1,1'-{[(bisalkane-1,N-diyl)]dioxy}bis[(11aS)-2,2-difluoro-7-methoxy-1,2,3-,11a-tetrahydro-5H-pyrrolo[2,1-c][1,4]benzodiazepine-5-one of formula VII (a-c).

4. A process as claimed in claim 3, wherein the dibromoalkane used in step (a) is selected from the group consisting of 1,3-dibromopropane, 1,4-dibromobutane and 1,5-dibromopentane.

5. A process as claimed in claim 3, wherein the dry organic solvent used in step (b) is selected from the group consisting of acetone, acetonitrile and DMF.

6. A process as claimed in claim 3, wherein mild inorganic base used in step (b) is selected from the group consisting of $K_2CO_3$, $CsCO_3$ and $BaCO_3$.

7. A process as claimed in claim 3, wherein the compound of formula V used in step(b) is selected from the group consisting of
- 1,1'-{[(Propane-1,3 diyl)dioxy]bis[2-nitro-5-methoxy-1,4-phenylene)carbonyl]}bis[4,4-difluoro-pyrrolidine-2-carboxaldehyde diethyl thioacetal (Va);
- 1,1'-{[Butane-1,4-diyl)dioxy]bis(2-nitro-5-methoxy-1,4-phenylene)carbonyl]}bis[4,4-difluoropyrrolidine-2-carboxaldehyde diethylthioacetal (Vb); and
- 1,1'-{[Pentane-1,5-diyl)dioxy]bis(2-nitro-5-methoxy-1,4-phenylene)carbonyl]}bis[4,4-difluoropyrroilidine-2-carboxaldehyde diethylthioacetal (Vc).

8. A process as claimed in claim 3, wherein the compound of formula VI obtained in step (c) is selected from the group consisting of 1,1'-{[(Propane-1,3diyl)dioxy]bis[2-amino-5-methoxy-1,4-pheny-lene)carbonyl]}bis[4,4-difluoropyrrolidine-2-carboxaldehyde diethylthioacetal (VIa);

1,1'-{[Butane-1,4-diyl)dioxy]bis(2-amino-5-methoxy-1,4-phenylene)carbonyl-]}bis[4,4-difluoropyrrolidine-2-carboxaldehyde diethylthioacetal (VIb); and 1,1'-{[Pentane-1,5-diyl)dioxy]bis(2-amino-5-methoxy-1,4-phenylene)carbonyl]}bis[4,4-difluoropyrrolidine-2-carboxaldehyde diethylthioacetal (VIc).

9. process as claimed in claim 3, wherein the organic solvent used in step (c) is ethyl acetate.

10. A process as claimed in claim 3, wherein the alkali bicarbonate used in step (c) is sodium bicarbonate.

11. process as claimed in claim 3, wherein the organic solvent used in step (c) is methanol.

12. process as claimed in claim 3, wherein the organic solvent used in step (d) is acetonitrile.

\* \* \* \* \*